(12) United States Patent
Zheng et al.

(10) Patent No.: US 12,404,487 B2
(45) Date of Patent: Sep. 2, 2025

(54) LACTOBACILLUS ACIDOPHILUS GOLDGUT-LA100 HAVING FUNCTIONS OF LIPID LOWERING, BLOOD GLUCOSE LOWERING AND WEIGHT LOSS AND APPLICATION THEREOF

(71) Applicant: Shenzhen Porshealth Bioengineering Co., Ltd., Shenzhen (CN)

(72) Inventors: Yanyi Zheng, Shenzhen (CN); Silu Zhang, Shenzhen (CN); Guoxun Xiao, Shenzhen (CN); Tengxun Zhang, Shenzhen (CN); Yuebiao Feng, Shenzhen (CN); Xin Teng, Shenzhen (CN); Song Huang, Shenzhen (CN)

(73) Assignee: Shenzhen Porshealth Bioengineering Co., Ltd., Shenzhen (CN)

( * ) Notice: Subject to any disclaimer, the term of this patent is extended or adjusted under 35 U.S.C. 154(b) by 0 days.

(21) Appl. No.: 18/919,965

(22) Filed: Oct. 18, 2024

(65) Prior Publication Data
US 2025/0043238 A1    Feb. 6, 2025

(30) Foreign Application Priority Data
Oct. 20, 2023  (CN) .......................... 202311375894.8

(51) Int. Cl.
*C12N 1/20* (2006.01)
*A61K 35/747* (2015.01)
*C12R 1/23* (2006.01)

(52) U.S. Cl.
CPC ............ *C12N 1/205* (2021.05); *A61K 35/747* (2013.01); *C12R 2001/23* (2021.05)

(58) Field of Classification Search
CPC .... C12N 1/205; A61K 35/747; C12R 2001/23
See application file for complete search history.

(56) References Cited

U.S. PATENT DOCUMENTS

| | | |
|---|---|---|
| 2012/0039852 A1 | 2/2012 | Darimont-Nicolau et al. |
| 2012/0114622 A1 | 5/2012 | Darimont et al. |
| 2013/0224168 A1 | 8/2013 | Darimont et al. |

OTHER PUBLICATIONS

CNIPA, Notification of First Office Action for Chinese application CN202311375894.8, May 17, 2024.
CNIPA, Notification to grant patent right for Chinese application CN202311375894.8, Jun. 12, 2024.

*Primary Examiner* — Louise W Humphrey
*Assistant Examiner* — Rachel Emily Martin
(74) *Attorney, Agent, or Firm* — Hemisphere Law, PLLC; Zhigang Ma

(57) ABSTRACT

The present invention relates to the technical field of microorganisms, in particular to a *Lactobacillus acidophilus* GOLDGUT-LA100 having functions of lipid lowering, blood glucose lowering and weight loss and application thereof. The *Lactobacillus acidophilus* GOLDGUT-LA100 provided by the present invention is preserved in China General Microbiological Culture Collection Center, with the preservation number of CGMCC No. 28398. The strain has strong acid resistance, can adapt to the digestive tract environment, and has high bile salt hydrolase activity. At the same time, in animal experiments, the strain significantly reduces blood glucose and serum cholesterol levels, reduces liver fat deposition, reduces adipose tissue inflammation, effectively reduces the weight, and has broad application prospects in the development of products for improving obesity, lowering lipid and lowering blood glucose.

1 Claim, 9 Drawing Sheets
Specification includes a Sequence Listing.

LACTOBACILLUS ACIDOPHILUS GOLDGUT-LA100 HAVING FUNCTIONS OF LIPID LOWERING, BLOOD GLUCOSE LOWERING AND WEIGHT LOSS AND APPLICATION THEREOF

SEQUENCE LISTING

The sequence listing is submitted as a XML file filed via EFS-Web, with a file name of "Sequence_Listing.XML", a creation date of Oct. 18, 2024, and a size of 3,650 bytes. The sequence Listing filed via EFS-Web is a part of the specification and is incorporated in its entirety by reference herein.

TECHNICAL FIELD

The present invention relates to the technical field of microorganisms, in particular to a *Lactobacillus acidophilus* GOLDGUT-LA100 having functions of lipid lowering, blood glucose lowering and weight loss and application thereof.

BACKGROUND

In recent years, the incidence of metabolic syndrome in humans has been increased globally, which increases the risk of coronary heart disease, stroke and other serious health problems. Obesity is a major factor that causes metabolic syndrome. Metabolic problems caused by obesity include hypertension, insulin resistance, type 2 diabetes, dyslipidemia and non-alcoholic fatty liver disease. With the improvement of the living standard of people and the change of lifestyles, the incidence of obesity has risen rapidly in the world, and has become a widely concerned health problem.

The main reason of obesity is the excess of energy intake over energy expenditure, and particularly related to the excessive intake of fats and refined carbohydrates. Before absorbed by the intestine, dietary fat is broken down into fatty acid, cholesterol and other products by the action of various enzymes and bile acids, and absorbed to enter the blood through the wall of the small intestine for the resynthesis of fat. In addition, when too much carbohydrate or sugar is taken in the diet, the excess sugar can also be converted into fat through a tricarboxylic acid cycle system. Excessive intake of the fat can cause an increase in serum cholesterol levels, and high cholesterol levels are an important factor that causes many cardiovascular diseases. Infiltrating macrophages in adipose tissue are associated with obesity-induced inflammation. The number of M1 macrophages is increased, proinflammatory cytokines are secreted, and inflammation is induced. Therefore, it is of great significance to reduce serum cholesterol levels and body fat percentage to prevent cardiovascular diseases.

The bile salt hydrolase (BSH) produced by intestinal bacteria can hydrolyze combined glycine bile salts and taurine bile salts into free bile salts and amino acid residues, thereby increasing the content of free bile salts in the intestinal cavity. Compared with the combined bile salts, the free bile salts have lower solubility and absorption efficiency. Therefore, the action of the BSH enables the reabsorption and the reuse of the bile salts, thereby increasing the synthesis of the bile salts in the liver. The synthesis of the bile salts in the liver requires the migration of cholesterol from the blood to the liver, thereby reducing the serum total cholesterol level. In addition, the lipid emulsifying capacity of the small intestine is limited, so the role of the BSH increases the excretion of dietary fat and cholesterol with feces. The BSH gene is widely present in lactic acid bacteria, such as *Lactobacillus* and *Bifidobacterium*, and has a deep exploration value in lowering cholesterol. Therefore, it is very necessary to screen lactic acid bacteria with high bile salt hydrolase activity.

SUMMARY

The present invention provides a *Lactobacillus acidophilus* GOLDGUT-LA100 having functions of lipid lowering, blood glucose lowering and weight loss and application thereof.

The present invention conducts isolation and screening from the intestinal tract of healthy human bodies to obtain a strain of *Lactobacillus acidophilus* having high bile salt hydrolase activity and the functions of strong cholesterol lowering, weight loss and blood glucose lowering. The strain has the potential to further develop and prepare probiotic products such as functional food having the effects of lipid lowering, blood glucose lowering and weight loss.

Specifically, the present invention provides the following technical solution:

The present invention provides a *Lactobacillus acidophilus* GOLDGUT-LA100. The strain was preserved in China General Microbiological Culture Collection Center (CGMCC for short, at Institute of Microbiology, Chinese Academy of Sciences, No. 3, Yard 1, Beichen West Road, Chaoyang District, Beijing, postcode: 100101) on Sep. 8, 2023, with the classified name of *Lactobacillus acidophilus* and the preservation number of CGMCC No. 28398.

The *Lactobacillus acidophilus* GOLDGUT-LA100 is isolated from the intestinal tract of a healthy human body, and is identified by bacterial morphology, physiology and 16S rDNA sequencing. The result is *Lactobacillus acidophilus*, named *Lactobacillus acidophilus* GOLDGUT-LA100. The strain has good gastric acid tolerance and high bile salt hydrolase activity. In animal experiments, the strain can effectively reduce the weight, blood glucose and serum cholesterol levels of mice, reduce liver fat deposition, and play a role of resisting adipose tissue inflammation by affecting the differentiation of macrophages, so as to achieve the effects of relieving inflammation and losing weight to provide bacteria resources for the development of dietary supplements, health care products and other food and drugs with weight loss effect.

The *Lactobacillus acidophilus* GOLDGUT-LA100 has the following microbiological characteristics:

(1) Morphological Features

Gram stain is positive, single or in pairs; colonies are formed on an MRS solid medium, which were milky white, smooth, convex, intact in edges, glittering and soft in texture.

(2) Physiological Characteristics

The *Lactobacillus acidophilus* GOLDGUT-LA100 can grow well under artificial gastric acid conditions, and has high bile salt hydrolase activity. In animal experiments, the *Lactobacillus acidophilus* GOLDGUT-LA100 can effectively reduce the body weight, blood glucose and serum cholesterol levels of mice, reduce the liver fat deposition, and alleviate adipose tissue inflammation.

The *Lactobacillus acidophilus* GOLDGUT-LA100 can be cultured by the following method: inoculating the strain in the medium and culturing at 35-37° C. for 12-24 h. The medium can adopt the conventional medium in the field, which can enable the *Lactobacillus acidophilus* GOLDGUT-LA100 to grow therein, and preferably adopts an MRS broth medium. The composition of the MRS broth medium is as follows: 10.0 g/L of casease digest, 10.0 g/L of beef powder, 4.0 g/L of yeast powder, 2.0 g/L of triammonium citrate, 5.0 g/L of sodium acetate, 0.2 g/L of magnesium sulfate, 0.05 g/L of manganese sulfate, 20.0 g/L of glucose, 2.0 g/L of dipotassium hydrogen phosphate and 1.0 g/L of Twain 80, with pH=5.7±0.2, and 1.5% agar is added to the solid medium.

After safety evaluation, virulence gene analysis of the strain shows that the strain does not contain virulence factors. The results of antibiotic resistance tests show that the strain does not contain transferable antibiotic resistance genes. The results of animal toxicity experiments show that the behavior and mental condition of mice are good. The strain belongs to an actual non-toxic level.

The present invention provides a microbial preparation comprising the *Lactobacillus acidophilus* GOLDGUT-LA100.

Preferably, in the microbial preparation, the *Lactobacillus acidophilus* GOLDGUT-LA100 is present in the form of live bacteria.

The above microbial preparation may be a solid preparation (such as bacterial powder) or a liquid preparation (such as emulsion preparation).

The present invention provides a preparation method of the above microbial preparation, comprising a step for culturing the *Lactobacillus acidophilus* GOLDGUT-LA100.

Preferably, the culture is conducted at 35-37° C.

Preferably, the culture is conducted in a liquid medium to obtain a bacteria solution.

The above bacteria solution may be prepared into a liquid preparation directly or by concentrating and/or adding other excipients, or prepared into a solid preparation by drying, or prepared into a solid preparation by separating bacterial bodies in the bacteria solution and then preparing the bacterial bodies.

Based on the function of the *Lactobacillus acidophilus* GOLDGUT-LA100, the present invention provides the following application of the strain:

The present invention provides an application of the *Lactobacillus acidophilus* GOLDGUT-LA100 or the microbial preparation in preparation of a product for producing bile salt hydrolases.

The present invention provides an application of the *Lactobacillus acidophilus* GOLDGUT-LA100 or the microbial preparation in preparation of a product for increasing the content of bile salt hydrolases in a body.

The present invention provides an application of the *Lactobacillus acidophilus* GOLDGUT-LA100 or the microbial preparation in production of bile salt hydrolases.

The present invention provides an application of the *Lactobacillus acidophilus* GOLDGUT-LA100 or the microbial preparation in preparation of a product that has the functions of lowering lipid, reducing liver fat deposition, and/or relieving adipose tissue inflammation.

Preferably, the lipid lowering is the lowering of cholesterol, preferably the lowering of serum total cholesterol.

Preferably, the relief of adipose tissue inflammation is achieved by improving the infiltration of macrophages in the fat.

The present invention provides an application of the *Lactobacillus acidophilus* GOLDGUT-LA100 or the microbial preparation in preparation of a product for lowering blood glucose.

The present invention provides an application of the *Lactobacillus acidophilus* GOLDGUT-LA100 or the microbial preparation in preparation of a product for weight loss.

Preferably, the weight loss is to inhibit weight gain and/or reduce weight.

Preferably, the action objects of the product for weight loss are high-fat diet animals, which may be healthy or obese animals.

In the above application, the product is food, a drug, a feed or a feed additive.

The present invention provides an application of the *Lactobacillus acidophilus* GOLDGUT-LA100 or the microbial preparation in preparation of food, a drug, a feed or a feed additive.

In the present invention, the food comprises ordinary food, dietary supplements and health products.

The present invention provides a product comprising the *Lactobacillus acidophilus* GOLDGUT-LA100 or the microbial preparation; and the product is food, a drug, a feed or a feed additive.

In addition to comprising the *Lactobacillus acidophilus* GOLDGUT-LA100 or the microbial preparation, the food may also comprise raw materials permitted in the field of food. The food may be dietary supplements, health products or fermented food.

In addition to comprising the *Lactobacillus acidophilus* GOLDGUT-LA100 or the microbial preparation, the drug may also comprise ingredients (e.g., fillers, excipients, lubricants, wetting agents, diluents, etc.) permitted in the field of pharmacy. The preparation type of the drug may be a solid preparation (e.g. powder, granule, capsule, tablet, etc.) or a liquid preparation (e.g. oral liquid, etc.).

The beneficial effects of the present invention include at least: the *Lactobacillus acidophilus* GOLDGUT-LA100 provided by the present invention has strong acid resistance, can adapt to the digestive tract environment, and has high bile salt hydrolase activity. At the same time, in animal experiments, the *Lactobacillus acidophilus* GOLDGUT-LA100 significantly reduces blood glucose and serum cholesterol levels, reduces liver fat deposition, reduces adipose tissue inflammation, effectively reduces the weight, and has broad application prospects in the development of products for reducing weight or improving obesity, lowering lipid and lowering blood glucose.

DESCRIPTION OF DRAWINGS

To more clearly describe the technical solutions in the present invention or in the prior art, the drawings required to be used in the description of the embodiments or the prior art will be simply presented below. Obviously, the drawings in the following description are some embodiments of the present invention, and for those ordinary skilled in the art, other drawings can also be obtained according to these drawings without contributing creative labor.

In FIGS. 3 and 4, NCFM represents the control strain, and LA100 represents *Lactobacillus acidophilus* GOLDGUT-LA100.

In FIGS. 5, 6, 7, 8 and 9, ND represents a normal diet group, HFD represents a high-fat diet group, HFD+LA100 represents a *Lactobacillus acidophilus* GOLDGUT-LA100 intervention group, and HFD+orlistat represents a positive drug intervention group.

DETAILED DESCRIPTION

To make purposes, technical solutions and advantages of the present invention more clear, the technical solutions in the present invention will be clearly and fully described below in combination with the drawings in the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1 Isolation and Identification of *Lactobacillus acidophilus* GOLDGUT-LA100

Figure 1:
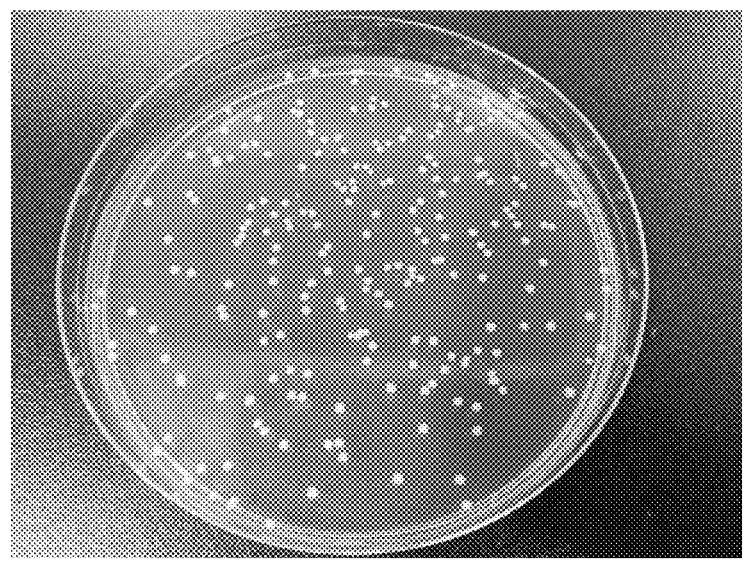
FIG. 1 shows the colony morphology of *Lactobacillus acidophilus* GOLDGUT-LA100 in embodiment 1 of the present invention.
Figure 2:
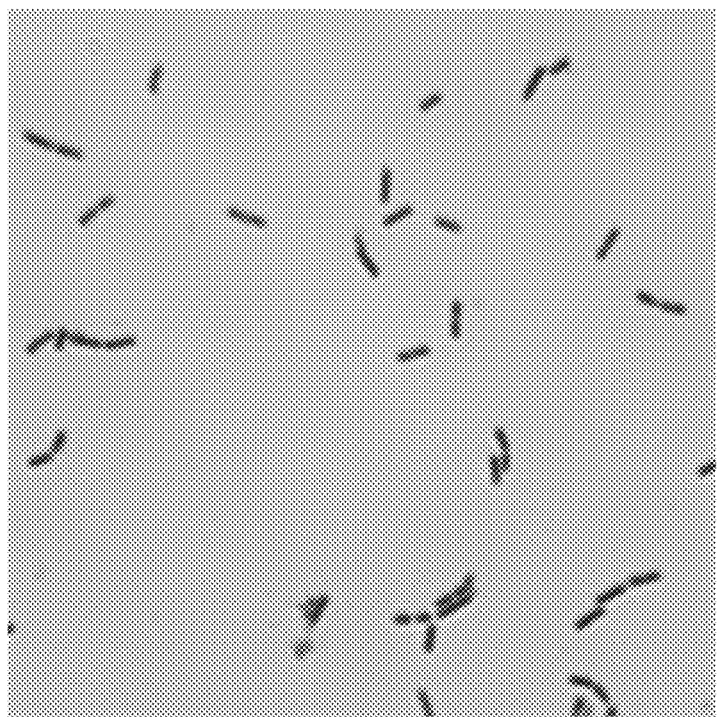
FIG. 2 shows the gram staining diagram of *Lactobacillus acidophilus* GOLDGUT-LA100 in embodiment 1 of the present invention with a magnification of 1000 times.

1. Isolation of *Lactobacillus acidophilus* GOLDGUT-LA100
1.1 Sample Source
The *Lactobacillus acidophilus* of the present invention is isolated from a healthy human gut.
1.2 Preparation of Medium
The medium used for sample isolation and strain screening is an MRS solid medium. The components of an MRS liquid medium are as follows: 10.0 g/L of casease digest, 10.0 g/L of beef powder, 4.0 g/L of yeast powder, 2.0 g/L of triammonium citrate, 5.0 g/L of sodium acetate, 0.2 g/L of magnesium sulfate ($MgSO_4 \cdot 7H_2O$), 0.05 g/L of manganese sulfate ($MnSO_4 \cdot 4H_2O$), 20.0 g/L of glucose, 2.0 g/L of dipotassium hydrogen phosphate, and 1.0 g/L of Twain −80, and 1.5% agar is added to prepare the MRS solid medium, with pH=5.7±0.2.
1.3 Isolation of Strains
1 g of sample was put into 10 mL of MRS liquid medium prepared in step 1.2, mixed evenly and then cultured at 36° C.; then 1 mL of enrichment solution is absorbed in a super clean bench for 10-fold gradient dilution; 100 μL of bacteria solution with $10^{-5}$, $10^{-6}$ and $10^{-7}$ dilution gradients was selected and coated on a petri dish containing the sterile MRS solid medium, and subjected to stationary culture at 36° C. under aerobic conditions for 24-48 h; and after obvious single colonies were formed, typical colonies were selected, and scribed and purified on the MRS solid plate medium for several times until the cultures with consistent colony morphology on the whole plate were identified for strains.
2. Identification of *Lactobacillus acidophilus* GOLDGUT-LA100
2.1 Colony Features
After the *Lactobacillus acidophilus* GOLDGUT-LA100 was cultured in the MRS solid medium for 24 h, the colonies were small, milky white, smooth, convex, intact in edges, glittering and soft in texture, as shown in FIG. 1.
2.2 Microscopic Morphology
The gram stain for *Lactobacillus acidophilus* GOLDGUT-LA100 is positive, single or paired, and V-shaped, as shown in FIG. 2.
2.3 16S rDNA Identification
Identification sequence: as shown in SEQ ID NO.1.
Identification results: According to the combination of the 16S rDNA sequence comparison results and physiological and biochemical results of the strain, the strain was determined to be *Lactobacillus acidophilus*.

*Lactobacillus acidophilus* GOLDGUT-LA100 was preserved in China General Microbiological Culture Collection Center (CGMCC for short, at Institute of Microbiology, Chinese Academy of Sciences, No. 3, Yard 1, Beichen West Road, Chaoyang District, Beijing, postcode: 100101) on Sep. 8, 2023, with the classified name of *Lactobacillus acidophilus* and the preservation number of CGMCC No. 28398.

Embodiment 2 Detection of Gastric Acid Tolerance of *Lactobacillus acidophilus* GOLDGUT-LA100

Figure 3:
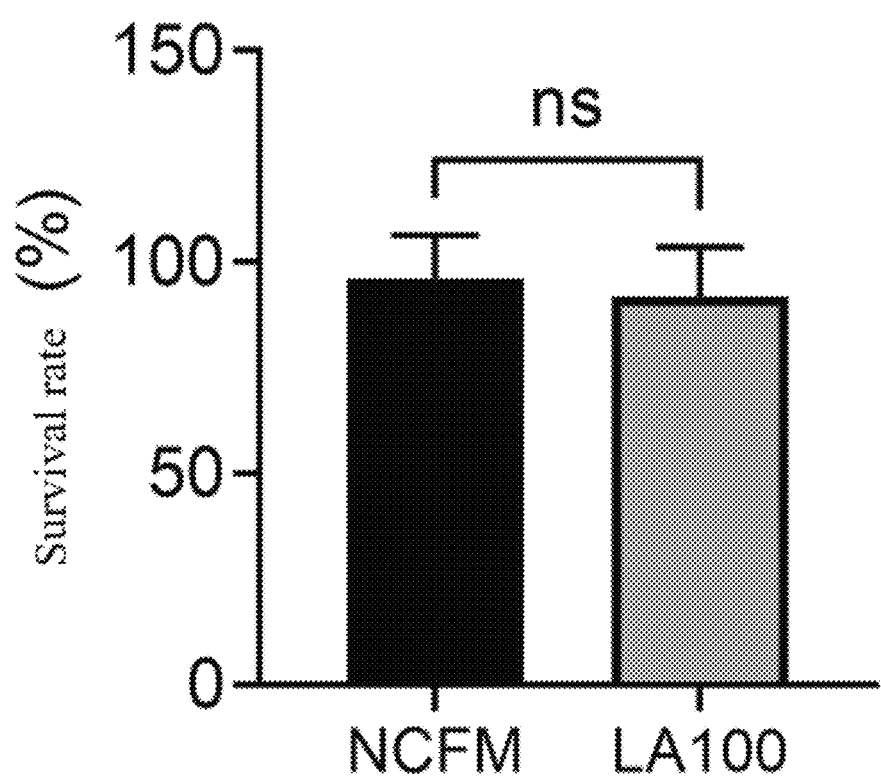
FIG. 3 shows the survival rate of *Lactobacillus acidophilus* GOLDGUT-LA100 and control strains in embodiment 2 of the present invention after cultured in artificial gastric acid for 2 h; the data are from three repeated experiments, and the error line represents the standard deviation.

The overall pH condition of the human stomach environment is strongly acidic, so the acid resistance of the strain is an important index to evaluate whether the strain can survive and colonize in the stomach acid environment. Artificial gastric juice was used to simulate the gastric environment. 100 μL of *Lactobacillus acidophilus* GOLDGUT-LA100 bacteria solution and 100 μL of simulated artificial gastric juice were blown and mixed evenly, and co-incubated anaerobically for 2 h at 37° C. Samples were taken at 0 h and 2 h respectively. The bacteria solution was diluted by 10-fold continuous gradient and coated on the MRS solid medium. After anaerobic culture at 37° C. for 48 h, colony count was performed, and the survival rate of the bacteria was calculated by a calculation formula: survival rate (%)=(2 h viable count/0 h viable count)×100%. The control strain was *Lactobacillus acidophilus* NCFM, which was a widely used edible probiotic strain with excellent acid resistance. It can be seen from FIG. 3 that *Lactobacillus acidophilus* GOLDGUT-LA100 has strong stomach acid tolerance, and the survival rate after treatment with artificial gastric juice is not significantly different from that of *Lactobacillus acidophilus* NCFM.

Embodiment 3 Determination of Bile Salt Hydrolase Activity of *Lactobacillus acidophilus* GOLDGUT-LA100

The present embodiment characterizes the activity of bile salt hydrolase by measuring the amount of amino acids (taurine and glycine) produced by catalyzing bile salt hydrolysis by bile salt hydrolase.

Figure 4:
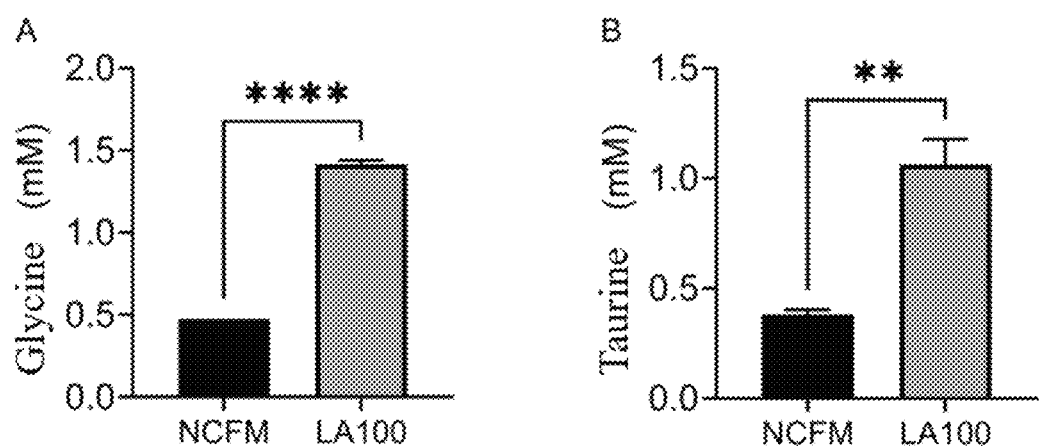
FIG. 4 shows the yields of glycine (A) and taurine (B) catalyzed by bile salt hydrolase of *Lactobacillus acidophilus* GOLDGUT-LA100 and control strains in embodiment 3 of the present invention; data are from three repeated experiments, and the error line represents the standard deviation; the statistical analysis method is Student's t-test;  represents that p value is less than 0.01, and ** represents that p value is less than 0.0001.

*Lactobacillus acidophilus* GOLDGUT-LA100 bacteria solution and the *Lactobacillus acidophilus* NCFM bacteria solution of the control strain were inoculated into 10 mL of MRS liquid medium with the inoculation ratio of 5% (v/v), and subjected to stationary anaerobic overnight culture at 37° C. for more than 16 h. The bacteria solution was centrifuged at 6000 rpm at 4° C. for 10 min; the supernatant was discarded; the bacteria were resuspended and washed by oscillating with the same volume of PBS, and centrifuged at 6000 rpm for 10 min. The washing operation was repeated twice, and the bacteria obtained by the last centrifugation was resuspended with 3 mL of PBS. After resuspension of the bacteria solution, the OD value of the bacteria solution was measured with a disposable colorimetric dish, and the same OD value was adjusted with ultrapure water. 3 mL of *Lactobacillus acidophilus* GOLDGUT-LA100 bacteria solution and the *Lactobacillus acidophilus* NCFM bacteria solution of the control strain with the same OD were taken into 10 mL centrifugal tubes, and 4 glass beads were added into each tube. Then, the centrifugal tubes were put into a tissue grinder to work at 70 Hz for 60 times (working for 20 s and stopping for 10 s). The ground sample was swirled, oscillated and mixed evenly. 1 mL was taken in a 2 mL centrifugal tube, and centrifuged at 12000 rpm at 4° C. for 5 min. The supernatant was collected. 950 µL of supernatant was taken into a 2 mL centrifugal tube; 50 µL of 0.4 M bile salt was added into the centrifugal tube; and the mixed system was heated in a water bath at 37° C. for 30 min. After the reaction, 500 µL of 15% trichloroacetic acid was added, swirled, oscillated, mixed evenly and centrifugated at 12000 rpm for 5 min. 200 µL of centrifugal supernatant was taken into a 10 mL centrifugal tube; 1 mL of ninhydrin reaction solution and 1 mL of 0.5M citric acid buffer (pH=5.5) were added into the centrifugal tube, swirled, oscillated, mixed evenly, and heated in a boiling water bath for 30 min until the color of the system was stable. The system after the boiling water bath was cooled in cold water, 2.8 mL of 70% ethanol was added to the system, and the system was swirled, oscillated and mixed evenly. The sample was transferred to a 96-well plate with 200 µL per well, and the sample $OD_{570}$ was measured by a microplate reader and the data were recorded. The absorbance values obtained were substituted into the standard curves of glycine and taurine to calculate the production of two amino acids. It can be seen from FIG. 4 that, compared with the control strain group, *Lactobacillus acidophilus* GOLDGUT-LA100 group produces more glycine and taurine, which proves that the bile salt hydrolase activity of *Lactobacillus acidophilus* GOLDGUT-LA100 was higher than that of the control strain.

Embodiment 4 Weight Loss Effect of *Lactobacillus acidophilus* GOLDGUT-LA100 in a Mouse Model C57BL/6 mice aged 4-6 weeks were randomly divided into a high-fat diet (HFD) group and a normal diet (ND) group. Each group was provided with different diet types. The diet of the HFD group was 20% of kcal protein, 20% of kcal carbohydrate and 60% of kcal fat, with 5.24 kcal/g. The diet of the ND group was 20.6% of kcal protein, 67.4% of kcal carbohydrate and 12% of kcal fat, with 3.64 kcal/g. Weight was measured weekly and each group was fed for 7 weeks. Obese modeling mice were selected from the HFD group according to the standard that the average weight of mice was higher by 20% than the ND group, and intervention experiments were carried out.

The obese modeling mice were divided into three groups: HFD+GOLDGUT-LA100 groups were given probiotic gavage intervention, that is, *Lactobacillus acidophilus* GOLDGUT-LA100 resuspended with normal saline (2×10E9 CFU/mL, 500 µL/day/mouse) was used for gavage by a mouse gavage needle. HFD+orlistat groups were intervened with positive drug orlistat by gavage, i.e., orlistat dissolved with normal saline was gavaged by a mouse gavage needle (80 mg/kg/day, 500 µL/mouse). The HFD group was used as control group. The same amount of normal saline was gavaged. The intervention lasted for 7 weeks, during which all three groups were given the same high-fat diet. The ND group is used as a blank control group, and the mice were gavaged with the same amount of normal saline for 7 weeks and provided with the same normal diet. The weight was measured weekly.

Figure 5:
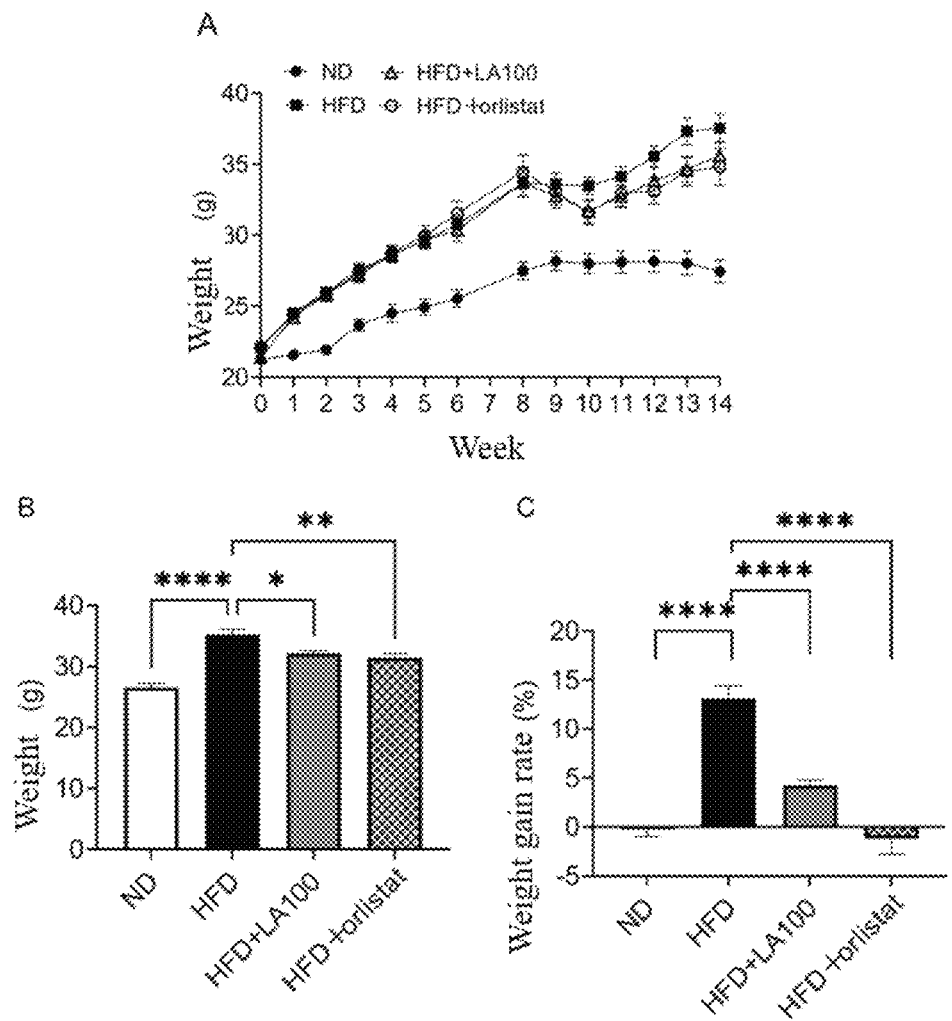
FIG. 5 shows the weight change of mice in each group in embodiment 4 of the present invention, wherein A shows the weight change of mice in four groups from week 1 to week 14; B shows the weight values of mice in four groups at week 14; C shows the weight gain rate of mice in four groups from week 8 to week 14; the error line represents the standard deviation; the statistical analysis method in B and C is one-way analysis of variance; * represents that p value is less than 0.05,  represents that p value is less than 0.01, and ** represents that p value is less than 0.0001.

A in FIG. 5 shows the 14-week weight change of the mice in four groups. Compared with the HFD control group, both the probiotic GOLDGUT-LA100 and the positive drug intervention significantly reduce the weight of the mice at week 14 (B in FIG. 5). According to the weight gain rate during the intervention (weight gain rate=(weight at week 14−weight at week 8)*100%/weight at week 8), the intervention of *Lactobacillus acidophilus* GOLDGUT-LA100 also significantly reduces the weight gain rate (C in FIG. 5). The above results show that the intervention of strain GOLDGUT-LA100 can slow the weight gain of obese mice induced by high-fat diet.

Embodiment 5 Effect of Lowering Blood Glucose by *Lactobacillus acidophilus* GOLDGUT-LA100 in a Mouse Model The mice in embodiment 4 were taken. After the intervention at week 14, trace blood samples were taken by a tail blood extraction method and blood glucose levels were measured with a glucose meter.

Figure 6:
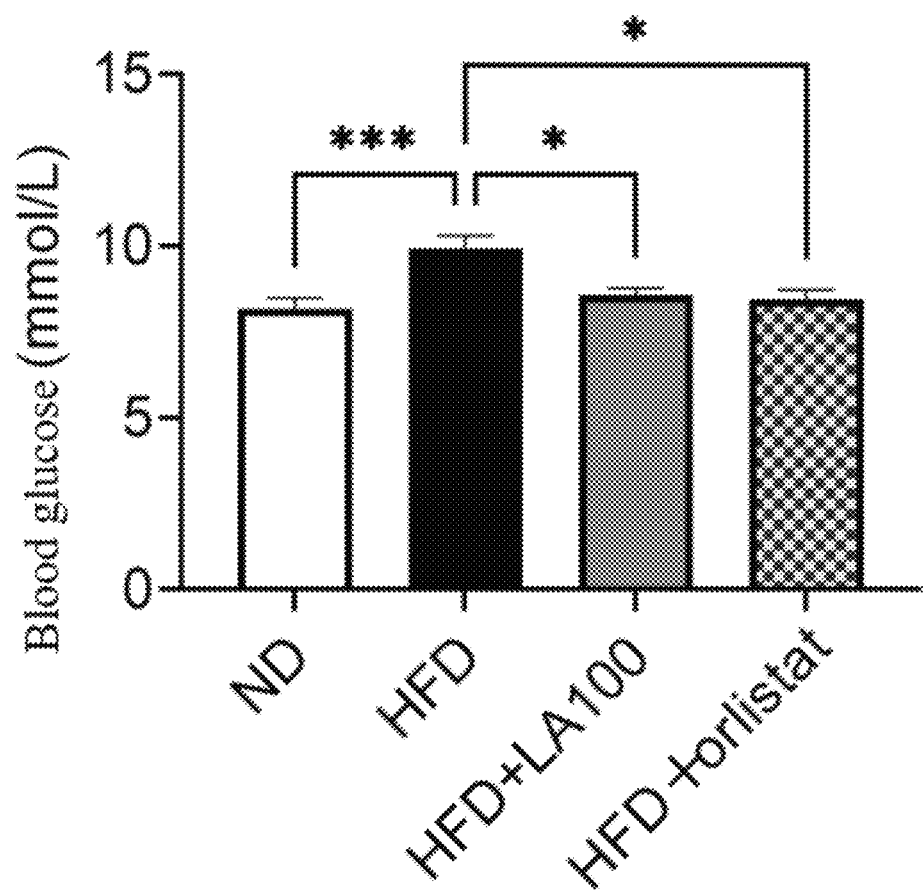
FIG. 6 shows the blood glucose values of mice in four groups after intervention in embodiment 5 of the present invention; the statistical analysis method is one-way analysis of variance; * represents that p value is less than 0.05 and *** represents that p value is less than 0.001.

The results show that the intervention of the probiotic GOLDGUT-LA100 lowers the blood glucose levels in the mice compared with the mice in the HFD group (FIG. 6).

Embodiment 6 Fat Reduction Effect of *Lactobacillus acidophilus* GOLDGUT-LA100 in a Mouse Model The mice in embodiment 4 were taken. After the intervention at week 14, blood was collected from the eyeballs to isolate the serum, and the total cholesterol content in the blood was detected by an automatic biochemical analyzer.

Figure 7:
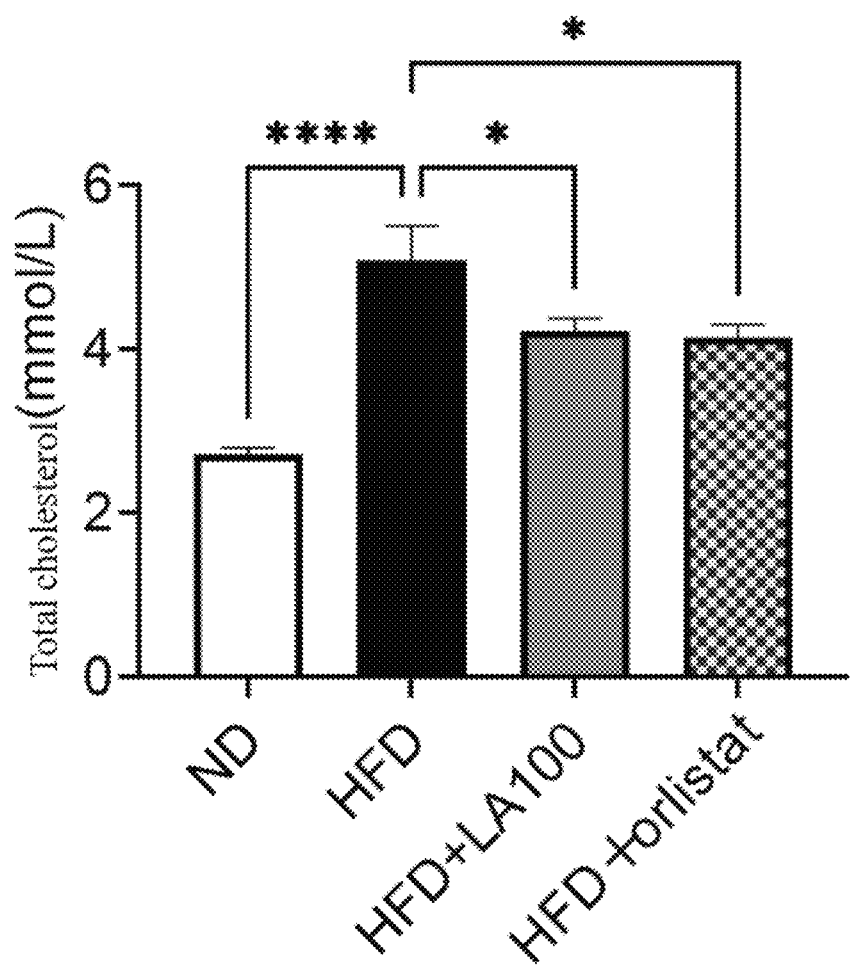
FIG. 7 shows the serum total cholesterol content of mice in four groups after intervention in embodiment 6 of the present invention; the statistical analysis method is one-way analysis of variance; * represents that p value is less than 0.05 and **** represents that p value is less than 0.0001.

The results show that the intervention of the probiotic GOLDGUT-LA100 reduces the total blood cholesterol content of the mice compared with the mice in the HFD group (FIG. 7).

Embodiment 7 Reduction of Liver Fat Deposition by *Lactobacillus acidophilus* GOLDGUT-LA100 in a Mouse Model The mice in embodiment 4 were taken. After the intervention at week 14, the liver was dissected, and tissue sections were made by cherry blossom embedding, stained with oil red O, observed with a microscope and photographed.

Figure 8:
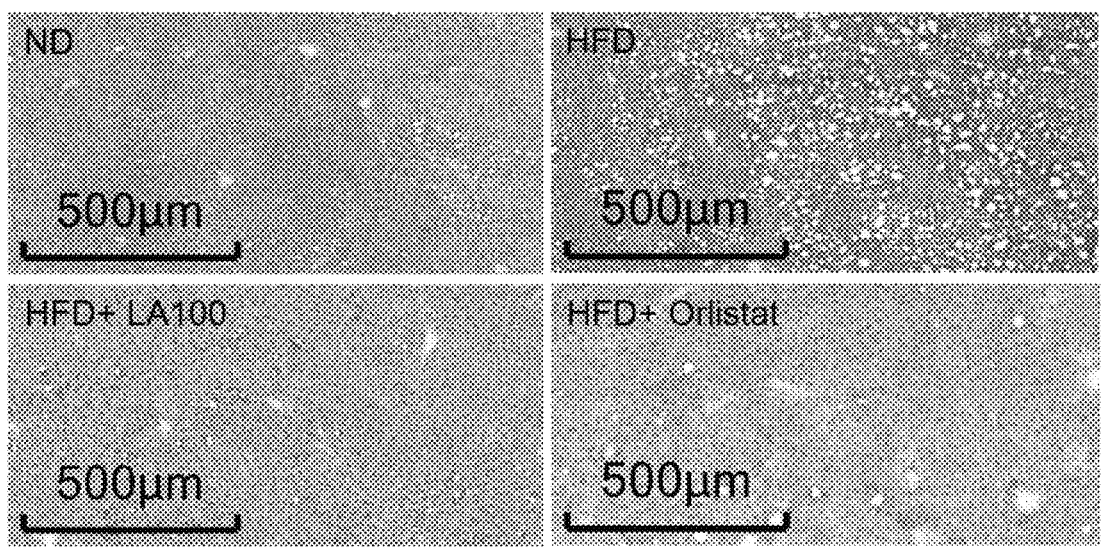
FIG. 8 shows the oil red O fat staining diagram of livers of mice in four groups after intervention in embodiment 7 of the present invention.

It can be seen from FIG. 8 that the high-fat diet causes the deposition of liver fat, and the intervention of the positive drug orlistat and probiotic GOLDGUT-LA100 has the effect of reducing liver fat deposition.

Embodiment 8 Improvement of Macrophage Infiltration in Fat in a Mouse Model by *Lactobacillus acidophilus* GOLDGUT-LA100

The mice in embodiment 4 were taken. After the intervention at week 14, the adipose tissue was cut into 2 mm×2 mm chunks with ophthalmic scissors; type II collagenase was added; the mixture was put in a water bath at 37° C. for 30 min; after the adipose tissue was digested into chylous shape, the adipose tissue was centrifuged at 1500 rpm for 5 min; the upper adipose tissue was discarded; and the cells were washed by PBS and resuspended. The adipose tissue resuspending cells after antibody staining were detected by a flow cytometry. Antibodies were selected as follows: an allophycocyanin anti-mouse F4/80 antibody, a peridinin chlorophyll protein anti-mouse CD11c antibody, and a fluorescein isothiocyanate anti-mouse CD11b antibody. F4/80+ CD11c+CD11b+ was defined as M1 macrophage; and F4/80+CD11c+CD11b− was defined as M2 macrophage. The infiltration of the macrophages in the adipose tissue was calculated by the flow cytometry.

Figure 9:
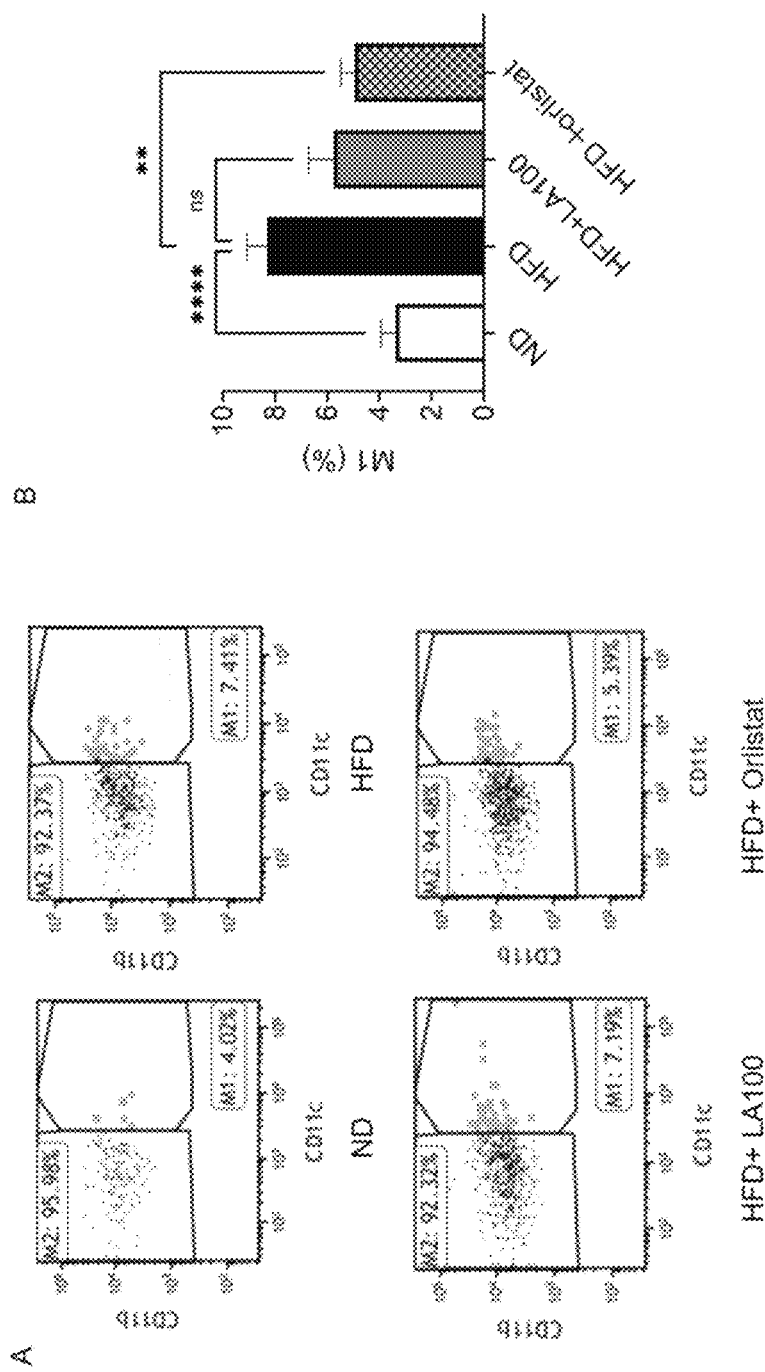
FIG. 9 shows the flow cytometry detection result diagram (A) and M1 macrophage quantitative result diagram (B) in embodiment 8 of the present invention; the statistical analysis method is one-way analysis of variance;  represents that p value is less than 0.01, ** represents that p value is less than 0.0001, and ns represents that there is no significant difference.

It can be seen from the flow cytometry detection results of A in FIG. 9 and the quantitative results of M1 macrophages in B in FIG. 9 that the positive drug orlistat significantly reduces the number of the M1 macrophages and reduces the inflammation of the adipose tissue. The intervention of the probiotic GOLDGUT-LA100 can also resist fatty inflammation induced by the high-fat diet.

In conclusion, the present invention obtains a strain of *Lactobacillus acidophilus* through isolation and screening, and the strain is named *Lactobacillus acidophilus* GOLDGUT-LA100. The strain can tolerate the artificial gastric acid environment and adapt to the digestive tract environment, and has high bile salt hydrolase activity. In vivo experiments in the mice demonstrate that the colonization of the strain can significantly reduce blood glucose and serum cholesterol levels, reduce liver fat deposition, reduce adipose tissue inflammation, and reduce the weight gain induced by the high-fat diet. Thus, the strain has broad application prospects in products for improving obesity, lowering lipid and lowering blood glucose.

Finally, it should be noted that the above embodiments are only used to illustrate the technical solutions of the present invention, not to limit the technical solutions. Although the present invention is described in detail by referring to the above embodiments, those ordinary skilled in the art shall understand that the technical solutions recorded in the above embodiments can be still amended, or some technical features therein can be replaced equivalently. These amendments or replacements do not enable the essence of the corresponding technical solutions to depart from the spirit and the scope of the technical solutions in the embodiments of the present invention.

What is claimed is:

1. A method of producing a microbial composition comprising *Lactobacillus acidophilus* with a deposit No. 28398 at the China General Microbiological Culture Collection Center (CGMCC No. 28398), wherein the method comprises:
  (a) inoculating a liquid preparation of *Lactobacillus acidophilus* CGMCC No. 28398 into MRS liquid media to form a mixture;
  (b) culturing the mixture at a temperature of 35-37° C.;
  (c) performing serial dilutions of the mixture to generate dilution gradients of $10^{-5}$, $10^{-6}$, and $10^{-7}$;
  (d) plating aliquots of each dilution onto a first MRS solid medium and incubating at 37° C. for 24 to 48 hours;
  (e) selecting isolated single colonies from the first MRS solid medium; and
  (f) repeatedly streaking the isolated colonies onto a second MRS solid medium to obtain purified strains.

* * * * *

SEQUENCE LISTING

```
Sequence total quantity: 1
SEQ ID NO: 1            moltype = DNA  length = 1436
FEATURE                 Location/Qualifiers
source                  1..1436
                        mol_type = genomic DNA
                        organism = Lactobacillus acidophilus
SEQUENCE: 1
tgcaagtcga gcgagctgaa ccaacagatt cacttcggtg atgacgttgg gaacgcgagc   60
ggcggatggg tgagtaacac gtggggaacc tgccccatag tctgggatac cacttggaaa  120
caggtgctaa taccggataa gaaagcagat cgcatgatca gcttataaaa ggcggcgtaa  180
gctgtcgcta tgggatggcc ccgcggtgca ttagctagtt ggtagggtaa cggcctacca  240
aggcaatgat gcatagccga gttgagagac tgatcggcca cattgggact gagacacggc  300
ccaaactcct acgggaggca gcagtaggga atcttccaca atggacgaaa gtctgatgga  360
gcaacgccgc gtgagtgaag aaggttttcg gatcgtaaag ctctgttgtt ggtgaagaag  420
gatagaggta gtaactggcc tttatttgac ggtaatcaac cagaaagtca cggctaacta  480
cgtgccagca gccgcggtaa tacgtaggtg gcaagcgttg tccggattta ttgggcgtaa  540
agcgagcgca ggcggaagaa taagtctgat gtgaaagccc tcggcttaac cgaggaactg  600
catcggaaac tgtttttctt gagtgcagaa gaggagagtg gaactccatg tgtagcggtg  660
gaatgcgtag atatatggaa gaacaccagt ggcgaaggcg gctctctggt ctgcaactga  720
cgctgaggct cgaaagcatg ggtagcgaac aggattagat accctggtag tccatgccgt  780
aaacgatgag tgctaagtgt tgggaggttt ccgcctctca gtgctgcagc taacgcatta  840
agcactccgc ctggggagta cgaccgcaag gttgaaactc aaaggaattg acgggggccc  900
gcacaagcgg tggagcatgt ggtttaattc gaagcaacgc gaagaacctt accaggtctt  960
gacatctagt gcaatccgta gagatacgga gttcccttcg gggacactaa gacaggtggt 1020
gcatggctgt cgtcagctcg tgtcgtgaga tgttgggtta agtcccgcaa cgagcgcaac 1080
ccttgtcatt agttgccagc attaagttgg gcactctaat gagactgccg gtgacaaacc 1140
ggaggaaggt ggggatgacg tcaagtcatc atgcccctta tgacctgggc tacacacgtg 1200
ctacaatgga cagtacaacg aggagcaagc ctgcgaaggc aagcgaatct cttaaagctg 1260
ttctcagttc ggactgcagt ctgcaactcg actgcacgaa gctggaatcg ctagtaatcg 1320
cggatcagca cgccgcggtg aatacgttcc cgggccttgt acacaccgcc cgtcacacca 1380
tgggagtctg caatgcccaa agccggtggc ctaaccttcg ggaaggagcc gtctaa     1436
```